(12) United States Patent
Briggs

(10) Patent No.: US 7,534,616 B2
(45) Date of Patent: May 19, 2009

(54) UNINTERRUPTED FLOW PUMP APPARATUS AND METHOD

(75) Inventor: Dennis A. Briggs, West Chester, PA (US)

(73) Assignee: Therakos, Inc., Exton, PA (US)

( * ) Notice: Subject to any disclaimer, the term of this patent is extended or adjusted under 35 U.S.C. 154(b) by 187 days.

(21) Appl. No.: 10/290,411

(22) Filed: Nov. 8, 2002

(65) Prior Publication Data

US 2003/0065284 A1 Apr. 3, 2003

Related U.S. Application Data

(63) Continuation of application No. 09/389,463, filed on Sep. 3, 1999, now Pat. No. 6,495,366.

(51) Int. Cl.
*A61M 37/00* (2006.01)
(52) U.S. Cl. .......................... 436/16; 422/99; 422/100; 422/101; 604/6.01; 604/6.02; 210/782
(58) Field of Classification Search .................. 436/16; 422/99–101, 106, 112; 604/5, 6.01–6.02, 604/6.03, 6.04, 6.08, 20, 245; 210/782, 646, 210/748; 222/70, 389
See application file for complete search history.

(56) References Cited

U.S. PATENT DOCUMENTS

| | | | |
|---|---|---|---|
| 3,756,459 A * | 9/1973 | Bannister et al. ................ 222/1 |
| 4,041,944 A * | 8/1977 | Rhodes ........................ 604/6.1 |
| 4,043,332 A | 8/1977 | Metcalf |
| 4,048,994 A | 9/1977 | Lo |
| 4,132,644 A * | 1/1979 | Kolberg ........................ 210/85 |
| 4,191,181 A * | 3/1980 | Franetzki et al. ............. 604/151 |
| 4,196,281 A | 4/1980 | Hearst et al. |
| 4,227,420 A | 10/1980 | Lamadrid |
| 4,321,919 A | 3/1982 | Edelson |
| 4,332,246 A | 6/1982 | Thomson |
| 4,398,906 A | 8/1983 | Edelson |
| 4,428,744 A | 1/1984 | Edelson |
| 4,430,078 A | 2/1984 | Sprague |
| 4,452,811 A | 6/1984 | della Valle |
| 4,464,166 A | 8/1984 | Edelson |
| 4,464,354 A | 8/1984 | Bisagni et al. |
| 4,465,691 A | 8/1984 | Bisagni et al. |
| 4,469,593 A | 9/1984 | Ishihara et al. |
| 4,568,328 A | 2/1986 | King |
| 4,573,960 A | 3/1986 | Goss |

(Continued)

FOREIGN PATENT DOCUMENTS

EP 0 094 682 11/1983

(Continued)

OTHER PUBLICATIONS

Lee et al., Yale J. Biol. Med. 621-28 (1989).

(Continued)

*Primary Examiner*—Jill Warden
*Assistant Examiner*—Jyoti Nagpaul
(74) *Attorney, Agent, or Firm*—Woodcock Washburn LLP

(57) ABSTRACT

This invention describes a method for pumping or delivering fluids utilizing a flexible vessel subject to controlled pressures within another pressure vessel. The pressure vessel can be sourced with positive and/or negative (e.g., vacuum) pressure.

5 Claims, 12 Drawing Sheets

U.S. PATENT DOCUMENTS

| | | | |
|---|---|---|---|
| 4,573,961 A | 3/1986 | King | |
| 4,573,962 A | 3/1986 | Troutner | |
| 4,573,992 A | 3/1986 | Marx | |
| 4,578,056 A | 3/1986 | King et al. | |
| 4,586,920 A | 5/1986 | Peabody | |
| 4,596,547 A | 6/1986 | Troutner | |
| 4,600,401 A | 7/1986 | Kamen | |
| 4,612,007 A | 9/1986 | Edelson | |
| 4,613,322 A | 9/1986 | Edelson | |
| 4,619,652 A | 10/1986 | Eckenhoff et al. | |
| 4,623,328 A | 11/1986 | Hartranft | |
| 4,642,088 A | 2/1987 | Guenter | |
| 4,643,710 A | 2/1987 | Troutner | |
| 4,657,160 A | 4/1987 | Woods et al. | |
| 4,666,430 A | 5/1987 | Brown et al. | |
| 4,681,568 A | 7/1987 | Troutner | |
| 4,683,889 A | 8/1987 | Edelson | |
| 4,684,521 A | 8/1987 | Edelson | |
| 4,687,464 A | 8/1987 | Troutner | |
| 4,692,138 A | 9/1987 | Troutner et al. | |
| 4,693,981 A | 9/1987 | Wiesehahn et al. | |
| 4,696,670 A | 9/1987 | Ohnishi et al. | |
| 4,705,498 A | 11/1987 | Goss | |
| 4,708,715 A | 11/1987 | Troutner et al. | |
| 4,726,949 A | 2/1988 | Miripol et al. | |
| 4,727,027 A | 2/1988 | Wiesehahn et al. | |
| 4,737,140 A * | 4/1988 | Lee et al. | 604/6.08 |
| 4,748,120 A | 5/1988 | Wiesenhahn | |
| D298,279 S | 10/1988 | Lee et al. | |
| 4,778,451 A | 10/1988 | Kamen | |
| D298,567 S | 11/1988 | Morris | |
| D299,531 S | 1/1989 | Troutner et al. | |
| D299,953 S | 2/1989 | King et al. | |
| 4,808,161 A | 2/1989 | Kamen | |
| 4,826,482 A | 5/1989 | Kamen | |
| 4,838,852 A * | 6/1989 | Edelson et al. | 604/6.01 |
| 4,866,282 A | 9/1989 | Miripol et al. | |
| 4,897,789 A | 1/1990 | King et al. | |
| 4,921,473 A | 5/1990 | Lee et al. | |
| 4,923,449 A * | 5/1990 | Toya et al. | 604/245 |
| 4,952,812 A | 8/1990 | Miripol et al. | |
| 4,955,860 A | 9/1990 | Ruano | |
| 4,960,408 A | 10/1990 | Klainer et al. | |
| 4,976,162 A | 12/1990 | Kamen | |
| 4,976,707 A * | 12/1990 | Bodicky et al. | 604/408 |
| 4,999,375 A | 3/1991 | Bachynsky et al. | |
| 5,013,303 A | 5/1991 | Tamari et al. | |
| 5,030,200 A | 7/1991 | Judy et al. | |
| 5,088,515 A | 2/1992 | Kamen | |
| 5,090,963 A | 2/1992 | Gross et al. | |
| 5,106,374 A | 4/1992 | Apperson et al. | |
| 5,147,289 A | 9/1992 | Edelson | |
| 5,150,705 A | 9/1992 | Stinson | |
| 5,163,909 A | 11/1992 | Stewart | |
| 5,173,125 A | 12/1992 | Felding | |
| 5,176,921 A | 1/1993 | Wiesehahn et al. | |
| 5,178,182 A | 1/1993 | Kamen | |
| 5,193,990 A | 3/1993 | Kamen et al. | |
| 5,216,176 A | 6/1993 | Heindel et al. | |
| 5,288,605 A | 2/1994 | Lin et al. | |
| 5,308,309 A | 5/1994 | Morris | |
| 5,330,420 A | 7/1994 | Lee | |
| 5,344,568 A | 9/1994 | Kitaevich et al. | |
| 5,356,929 A | 10/1994 | Heindel et al. | |
| 5,360,734 A | 11/1994 | Chapman et al. | |
| 5,383,847 A | 1/1995 | Edelson | |
| 5,399,166 A | 3/1995 | Laing | |
| 5,401,342 A | 3/1995 | Vincent et al. | |
| 5,417,346 A | 5/1995 | Ferri, Jr. et al. | |
| 5,423,759 A | 6/1995 | Campbell | |
| 5,433,738 A * | 7/1995 | Stinson | 607/92 |
| 5,459,030 A | 10/1995 | Lin et al. | |
| 5,459,322 A | 10/1995 | Warkentin | |
| 5,482,193 A | 1/1996 | Fuchs | |
| 5,482,828 A | 1/1996 | Lin et al. | |
| 5,494,592 A | 2/1996 | Latham, Jr. et al. | |
| 5,533,978 A | 7/1996 | Teirstein | |
| 5,540,808 A | 7/1996 | Vincent et al. | |
| 5,569,928 A | 10/1996 | Lee et al. | |
| 5,578,005 A | 11/1996 | Sancoff et al. | |
| 5,651,993 A | 7/1997 | Edelson et al. | |
| 5,665,061 A | 9/1997 | Antwiler | |
| 5,690,396 A | 11/1997 | Johnston et al. | |
| 5,700,245 A | 12/1997 | Sancoff et al. | |
| 5,722,947 A | 3/1998 | Jeppsson et al. | |
| 5,733,253 A | 3/1998 | Headley et al. | |
| 5,733,257 A | 3/1998 | Sternby | |
| 5,776,104 A | 7/1998 | Guignard et al. | |
| 5,779,666 A | 7/1998 | Teirstein | |
| 5,785,681 A | 7/1998 | Indravudh | |
| 5,791,370 A | 8/1998 | Harland | |
| 5,792,367 A | 8/1998 | Mattisson et al. | |
| 5,800,383 A | 9/1998 | Chandler et al. | |
| 5,814,009 A | 9/1998 | Wheatman | |
| 5,830,181 A | 11/1998 | Thornton | |
| 5,843,037 A | 12/1998 | Uber, III | |
| 5,853,397 A | 12/1998 | Shemesh et al. | |
| 5,868,696 A | 2/1999 | Giesler et al. | |
| 5,873,853 A | 2/1999 | Keilman et al. | |
| 5,894,273 A | 4/1999 | Meador et al. | |
| 5,938,634 A | 8/1999 | Packard | |
| 5,984,887 A | 11/1999 | McLaughlin et al. | |
| 5,985,914 A | 11/1999 | Zeldis et al. | |
| 6,036,857 A | 3/2000 | Chen et al. | |
| 6,074,335 A | 6/2000 | Headley et al. | |
| 6,261,217 B1 * | 7/2001 | Unger et al. | 494/45 |
| 6,319,662 B1 * | 11/2001 | Foley et al. | 435/2 |
| 6,348,031 B1 * | 2/2002 | Unger et al. | 494/45 |
| 6,558,346 B1 * | 5/2003 | Yoshioka et al. | 604/67 |

FOREIGN PATENT DOCUMENTS

| | | |
|---|---|---|
| EP | 0 284 409 A2 | 9/1988 |
| EP | 0 289 048 A2 | 11/1988 |
| EP | 0 611 228 A2 | 8/1994 |
| EP | 0 704 224 A2 | 4/1996 |
| WO | WO 93/14791 | 8/1993 |
| WO | WO 95/03814 | 2/1995 |
| WO | WO 97/36581 | 10/1997 |
| WO | WO 97/36634 | 10/1997 |
| WO | WO 97/37536 | 10/1997 |
| WO | WO 98/22163 | 5/1998 |
| WO | WO 98/22164 | 5/1998 |
| WO | WO 98/22165 | 5/1998 |
| WO | WO 98/22167 | 5/1998 |

OTHER PUBLICATIONS

Therakos, Inc., "The UVAR XTS System: Engineering That Reflects Innovation" (1998).
Edelson et al., 316(6) N. Engl. J. Med. 297-303 (1987).
Margolis-Nunno et al., 35(10) Transfusion 855-62 (1995).
Hoofnagle et al., 315(25) N. Engl. J. Med. 1575-78 (1986).
Davis et al., 321(22) N. Engl. J. Med. 1501-05 (1989).
Di Bisceglie et al., 321(22) N. Engl. J. Med. 1506-10 (1989).
Farci et al., 325(2) N. Engl. J. Med. 98-104 (1991).
Shindo et al , 115(9) Ann. Int. Med. 700-04 (1991).
Gomez-Rubio et al., 11 J. Hepatol. S63-S67 (1990).
Saez-Royuela et al., 13(2) Hepatol. 327-31 (1991).
Nakano et al., 85(1) Amer. J. Gastroenterol. 24-29 (1990).
Hayashi et al., 89(7) Amer. J. Gastroenterol. 986-88 (1994).
Ljunggren et al., 74(1) J. Invest. Dermatol. 59-62 (1980).
Jansen et al., 33(2) Cufr. Ther. Res. 258-64 (1983).
Clemens et al., 226 Biochem. 345-60 (1985).
Witter et al., 44(2) Clin. Pharmacol. Ther. 239-43 (1988).

Rook et al., 127(10) Arch. Dermatol. 1535-40 (1991).
Rook et al., 62 Yale J. Biol. Med. 647-52 (1989).
Barr et al., "Immunomodulation with Photopheresis: Clinical Results of the Multi-Center Cardiac Transplantation Study".
Costanzo-Nordin et al., 53(4) Transplantation 808-15 (1992).
Meiser et al., 57(4) Transplantation 563-68 (1994).
Vowels et al., J. Invest. Dermatol. 686-92 (1992).
Campbell et al., "HCV RNA Peripheral Blood Mononuclear Cells of Chronic Hepatitis C Patients Treated with Interferon Alfa-2b: Another Possible Indicator of Response?".
Gil et al., 18(5) Hepatol. 1050-54 (1993).
Qian et al., 16 J. Hepatol. 380-83 (1992).
Mendoza et al., 174 J. Infect. Dis. 842-44 (1996).
Zignego et al., 15 J. Hepatol. 382-86 (1992).
Shirai et al., J. Virol. 4098-106 (1992).
Kanai et al., 336 Lancet 245 (1990).
Weiner et al., 89 Proc. Natl. Acad. Sci. USA 3468-72 (1992).
Garson et al., 336 Lancet 878-79 (1990).
Shimizu et al., 87 Proc. Natl. Acad. Sci. USA 6441-44 (1990).
Simmonds et al., 74 J. Gen. Virol. 2391-99 (1993).

Houghton et al., 14(2) Hepatol. 381-88 (1991).
Choo et al., 88 Proc. Natl. Acad. Sci. USA 2451-55 (1991).
Koretz et al., 88(5) Gastroenterol. 1251-54 (1985).
Dienstag, 85(2) Gastroenterol. 439-62 (1983).
Choo et al., 244 Science 359-62 (1989).
16 Progress 1-12 (1994).
Watson et al., 28 Ann. Pharmacother. 341-42 (1994).
Rossetti et al., 59(1) Transplantation 149-51 (1995).
Rook et al., 128 Arch. Dermatol. 337-46 (1992).
Malawista et al., 34(6) Arth. Rheumat. 646-54 (1991).
Edelson, Ann. NY Acad. Sci. 154-64.
Grass et al . 91(6) Blood 2180-88 (1998).
Bisaccia et al., 113(4) Ann. Int. Med. 270 (1990).
Bisaccia et al., 6 J. Aids 386 (1993).
Dall'Amico et al., 97 Brit. J. Haematol. 848 (1997).
Edelson et al., 4(5) Biol. Ther. Can. 1 (1994).
Greinix et al., 92(9) Blood 3098 (1998).
Zic et al., 35(6) J. Amer. Acad. Dermatol. 935 (1996).

* cited by examiner

UNINTERRUPTED FLOW PUMP APPARATUS AND METHOD

CROSS REFERENCE TO RELATED APPLICATIONS

This application is a continuation of U.S. patent application Ser. No. 09/389,463, filed Sep. 3, 1999, now U.S. Pat. 6,495,366.

BACKGROUND OF THE INVENTION

1. Field of the Invention

The present invention relates to a method and apparatus for pumping or delivering fluids utilizing a flexible vessel that may be subject to controlled pressures and preferably located within a pressure vessel.

2. Description of the Prior Art

Current methods for pumping or delivering fluids, particularly biological fluids, include utilizing peristaltic (tubing) pumps, diaphragm pumps, and centrifugal pumps. Biological fluids encompass fluids that comprise, exist in or are used in or delivered to living organisms. Indeed, biological fluids may comprise pharmaceutical preparations (e.g., insulin, erythopoietin, or morphine) or biological preparations (e.g., liposomes, plasmids, naked DNA or transformed cells), bodily fluids and their components, such as blood cells, and other fluids that comprise biological components, including living organisms such as bacteria, cells or other cellular components. Biological fluids also may comprise whole blood or specific whole blood components, including red blood cells, platelets, buffy coat, white blood cells, precursor cells, progenitor cells; prokaryotic and eukaryotic cell suspensions, including recombinant, transformed, and transfected cells; viruses and viral preparations including recombinant viruses; membrane vesicle preparations, including lysosomes, endosomes, caveolae, micelles, and liposomes; molecule interactions including DNA-protein, RNA-protein, and protein-protein interactions; DNA preparations; RNA preparations; and protein preparations.

Certain fluid types, such as fluids comprising pressure or flow sensitive fluids, such as biological fluids, can be negatively affected by subjecting such fluids to such current pumping or delivering methods. For example, biological fluids comprising blood or its cellular components, may be damaged (e.g., cells may be lysed or membranes damaged) when exposed to perturbations and/or turbulence caused by such current methodologies. Moreover, these fluid types may also be negatively affected by inaccurate or inconsistent flow rates and pressures created by such current methods. In addition, drug delivery systems are negatively affected by such inaccurate or inconsistent flow rates.

One of the specific drawbacks, for example, with peristaltic pumps is that they are essentially positive displacement and have the potential to develop excessive pressures if an occlusion occurs within the pump or its components. When pumping or delivering biological fluids, such as whole blood or buffy coat, any excess pressure resulting from even a partial occlusion may result in cell membrane damage or hemolysis. Diaphragm pumps present difficulties in the measurement of fluid volume pumped when partial strokes are involved and may require auxiliary valving. Centrifugal pumps are difficult to track for volume pumped, cannot hold against a static head without check valves, are non-reversible, and generally require some mechanical rotor support in the fluid stream (e.g., a hydrodynamic bearing or magnetic system). The diaphragm and centrifugal pump types also have more complex disposable elements than the peristaltic type pumps. In the drug delivery area, devices such as the hypodermic syringe that deliver a bolus of a drug or other active agent also present difficulties since the bolus must be gradually absorbed and delivered throughout the patient's body, which is a process subject to many individual variances.

The Kamen family of pump technology (e.g., U.S. Pat. Nos. 4,600,401, 4,778,451, 4,808,161, and 5,193,990) in some respects attempt to solve some of the problems of the peristaltic pump, however, Kamen-type pumps have their own drawbacks. Kamen described a fluid movement technology based on the use of pneumatically driven diaphragm pumps and valves controlled by computer calculations of stroke volume displacement as a function of pressure and temperature. These calculations are time consuming and necessarily precise because the stroke volumes are small and the cumulative error must be kept minimal. Each stroke is interrupted by a long static period during which these measurements are made. In order to maintain the required average flow rate, the actual flow rate must be high, resulting in a step type of flow (a jump up when restarting the flow) which is detrimental, for example, to sensitive fluids in general, to many biological fluids, and to most types of cell separation processes, particularly the "skimming" type cell separation processes commonly used in conjunction with centrifuges. (In a skimming operation, discontinuous flow and the jump of restarting flow, for example, in a photopheresis process, disturbs cell separation causing a flood of red blood cells in a plasma stream.) To compensate for the inefficiencies caused by discontinuous flow in a system using a Kamen-type pump, and its impact on, for example, a separation type process, additional fluid flow must be processed and procedure times increased.

Additionally, the Kamen family of pump technology requires a rigid disposable pumping or delivering/valving module which contains valve chambers that interrupt the laminar nature of flow in tubing, causing undesired mixing of separated components as the front flows through. This module (or cassette) is also typically costly and complicated to manufacture.

The present invention differs from the prior art, in that it allows, for example, for pressurized flow of a fluid without a pause in pumping or delivering. The present invention, in contrast to the Kamen pump family described above, allows, for example, for one continuous flow (i.e., "push") of fluid. The costly and complicated Kamen disposable pump/valve is eliminated. The present invention can be operated at much higher constant flow rates and average flow rates without the risk of high restart flow introduced in the Kamen system, as well as others, to catch up the average flow rate due to the pause and its related reduction in flow rate. The discontinuity and inefficiencies of the Kamen-type system and others are, therefore, addressed by the present invention.

Additionally, the present invention, in contrast to the centrifugal type pump, is or can be configured to be reversible. The present invention can also operate at a constant or modulated pressure to avoid the potential inherent in the peristaltic and other types of pump systems to develop excessive pressures, for instance, during an occlusion of the flow. The volume and other parameters of the fluid flow are accurately measurable in the present invention, in contrast to the diaphram and centrifugal-type pump systems. The present invention may include, for example, a pressure limiting pump or direct weight measurement rather than a flow rate controlled pump, for added safety if a line associated with the pump becomes blocked or occluded. The present invention can also incorporate a minimal amount of noncomplex disposable elements and yet maintain, if desirable, the sterility of the pumping or delivering operation. Such sterility and minimized complexity may be particularly desirable when manipulating biological fluids such as pharmaceuticals and other active agents.

In comparison to pumps presently utilized in known processes or treatments, for example, the photopheresis and peritoneal dialysis processes described infra, the present invention can, for example: reduce total treatment or process time; reduce irradiation time (for photopheresis); allow increased flow rate; increase the total number of target cells collected or separated per total target cells processed (i.e., yield); increase the total number of target cells collected per treatment or process time; increase the total target cells collected per total volume of processed biologic fluid; reduce cell, fluid or fluid element damage in the process (e.g., reduced hemolysis); reduce contamination of target items collected (e.g., increase the percentage of target cells collected per total cells collected); operate with a reduced pressure differential; and, reduce flow rate differential.

SUMMARY OF THE INVENTION

The objects of the invention include providing a method and apparatus for providing a uniform and controlled flow of fluid. The invention relates to an apparatus and method for pumping or delivering fluids utilizing a flexible vessel subject to controlled pressures within an outer pressure chamber.

Certain of the objects of one or more embodiments of the present invention can, for example, in photopheresis and peritoneal dialysis procedures: reduce total treatment or process time; reduce irradiation time (for photopheresis); allow increased flow rate; increase the total number of target cells collected or separated per total target cells processed (i.e., yield); increase the total number of target cells collected per treatment or process time; increase the total target cells collected per total volume of processed biologic fluid; reduce cell, fluid or fluid element damage in the process (e.g., reduced hemolysis); reduce contamination of target items collected (e.g., increase the percentage of target cells collected per total cells collected); operate with a reduced pressure differential (i.e., reduce the variability of pressure in the system); and, reduce flow rate differential (i.e., reduce the variability of the flow rate in the system).

An additional object of one or more embodiments of the present invention is to reduce the amount of time that a patient's blood is outside the patient's body.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises a sealed flexible chamber adapted to contain a fluid or other pressure sensitive medium. This sealed flexible chamber can, for example, take the form of a plastic or other flexible bag, such as those typically used for storing and transferring sterile fluids, such as sterile biological fluids. This sealed flexible chamber is then disposed within an outer chamber. The outer chamber can take many forms, including a more rigid bottle or other housing and may be made of a myriad of materials including glass, plastic and the like.

The flexible chamber is part of a fluid path that extends beyond the exterior of the outer chamber by, for example, a catheter or other tube-like or other cannulated structure. The outer chamber is situated and constructed such that it can contain a pressure sensitive medium such as a gas or other fluid, such as air, for example, which can exert pressure on the flexible chamber.

This apparatus and method may include a means for increasing or decreasing pressure in a uniform and controlled manner within the space around the flexible chamber. Such means for increasing or decreasing pressure includes, for example, exposing the flexible chamber to reservoirs of gas or other pressurized fluids regulated at specific pressures or vacuum levels, or can take the form, for example, of any one of a myriad of standard pressurization pumps.

The disclosed method for pumping or delivering fluids includes changing the pressure within the space around the sealed flexible chamber such that fluid is displaced into or out of the sealed chamber in a uniform and controlled manner without or within the sealed flexible chamber.

The present invention and its preferred embodiments are particularly useful in the controlled flow of pressure sensitive fluids, such as, for example, certain biological fluids, and more specifically, in the controlled flow of blood or its cellular components.

The present invention also may include, in one or more embodiments, monitoring the increasing or decreasing pressure within the space around the sealed flexible chamber. The present invention may also include monitoring the volume, mass, weight or other properties of fluid displaced from or transferred into a flexible chamber. The present invention also may include, in one or more embodiments, the pressure sensitive medium of air or a gas about the flexible chamber disposed in the outer chamber.

In one embodiment of the present invention, the flexible chamber is filled with a fluid and that fluid is pushed, by applying pressure, into the environment outside of the outer chamber which may be, for example, a patient, or another chemical or manufacturing processor, by continuous means. The fluid flow is accomplished by the application of pressure into the outer chamber on the flexible chamber. The source of the pressure can be any standard pressure reservoir that is different (either greater or less than) the pressure surrounding the flexible chamber. If the pressure applied is less than that surrounding the flexible chamber (i.e., a vacuum), then the flexible chamber will displace the fluid out of the environment found outside of the outer chamber and into the flexible chamber. Conversely, if the pressure applied is more than that surrounding the flexible chamber, then the flexible chamber will displace the fluid out of the flexible chamber and into the environment found outside of the outer chamber. The present invention preferably accomplishes fluid flow without any discontinuity or disruption of flow until the source of fluid is depleted, the flexible chamber is completely filled or emptied, or until the differential in pressure around the flexible chamber is eliminated.

An additional advantage in one or more embodiments of the present invention, over the prior art, is that the flexible chamber obtaining or providing the fluid need not be maintained in a sterile environment for the process and fluid itself to be kept sterile. So long as the inside surface of the flexible chamber and the fluid itself are sealed off of the outside environment, the system will be sterile regardless of the environment outside of the flexible chamber.

The method of one of the preferred embodiments of the present invention disclosed herein, in the application of a separation system used in photophoresis or peritoneal dialysis systems as described supra, can perform the entire separation cycle with steady flow at regulated pressure through tubing uninterrupted by the sudden discontinuities of valve chambers. Mass flow preferably may be monitored by continuous direct weight measurement. The disposable pumping or delivering/valving module of the Kamen system is, thereby, eliminated.

Indeed, the method and apparatus of an embodiment of the present invention, in comparison to the known Kamen-type pump technology used in the UVAR® XTS™ photopheresis system manufactured by Therakos, Inc., Exton, Pa., provide for one or more of: a reduction in total treatment or process time for the donor blood in the XTS™ system; a reduction in irradiation time of collected buffy coat in the system; an increased flow rate of whole blood into the system, as well as collected buffy coat out of the centrifuge of the XTS™ system; an increased total number of target cells (e.g., white blood cells) collected or separated per total white blood cells contained in the donor blood (i.e., yield); an increased total number of white blood cells collected per treatment or per unit process time; an increased number of total white blood cells collected per total volume of processed donor blood; a reduction of the contamination of collected white blood cells collected (e.g., an increase the percentage of white blood cells collected per total cells collected and/or decreasing the percent hematocirt in the collected buffy coat); and a reduced pressure differential and a reduced flow rate differential within the extracorporeal circuit.

In addition, the method and apparatus of an embodiment of the present invention, in comparison with the known peristaltic pump technology used in the UVAR® photopheresis system manufactured by Therakos, Inc., Exton, Pa., provide for a reduction in cell (red blood cell or white blood cell) damage (e.g., reduced hemolysis).

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

DESCRIPTION OF THE PREFERRED EMBODIMENTS

Reference will now be made in detail to the present preferred embodiments and exemplary embodiments of the invention, examples of which are illustrated in the accompanying drawings.

The present invention apparatus and method for pumping or delivering have a myriad of uses but are most advantageous for use when fluids, particularly biological fluids and pressure sensitive fluids, are pumped and/or when uninterrupted flow of the fluid is preferred. Such applications include biological and medical applications, for example, of photopheresis, cell separation, drug delivery and dialysis. This apparatus and method for pumping or delivering are also useful in providing for the movement of fluids in cyclical systems such as, for example, peritoneal dialysis, bypass and other blood flow processes. The present invention is also useful in other procedures involving the flow of fluids that are sensitive to changes in pressure and discontinuities in flow and has numerous applications in manufacturing pharmaceuticals, chemicals and other industrial processes.

Figure 1:
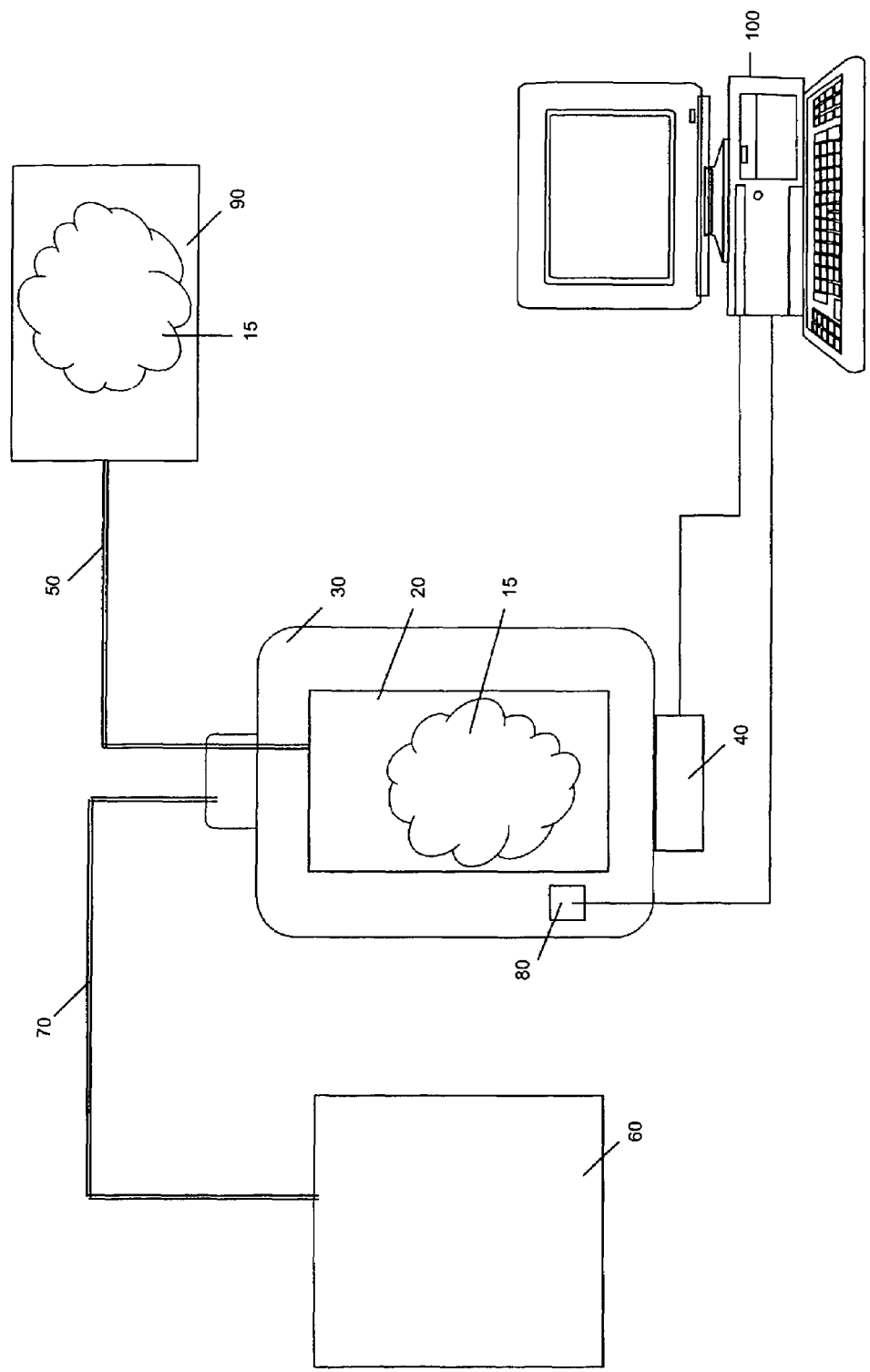
FIG. 1 is a schematic diagram of one embodiment of the present invention.

In accordance with the invention, as depicted in a particular embodiment, for example, in FIG. 1, the present invention can be accomplished by disposing a sealed flexible chamber 20 within an outer chamber 30. As explained above, this flexible chamber 20 can be any flexible sealed container. As depicted in FIG. 1, flexible chamber 20 is a flexible fluid container bag which can be disposable, however the invention is not limited to this type of bag and can comprise any type of sealed chamber or flexible membrane that can be compressed and/or expanded when pressure (or vacuum) is applied to it. The outer chamber 30 of FIG. 1 is depicted as a standard glass bottle but can be any pressure containing device or apparatus, including a plastic or other molded housing or other type container, such as, for example, might be used to house an entire pump system or other such medical device, or may be a molded plastic cassette.

Figure 2:
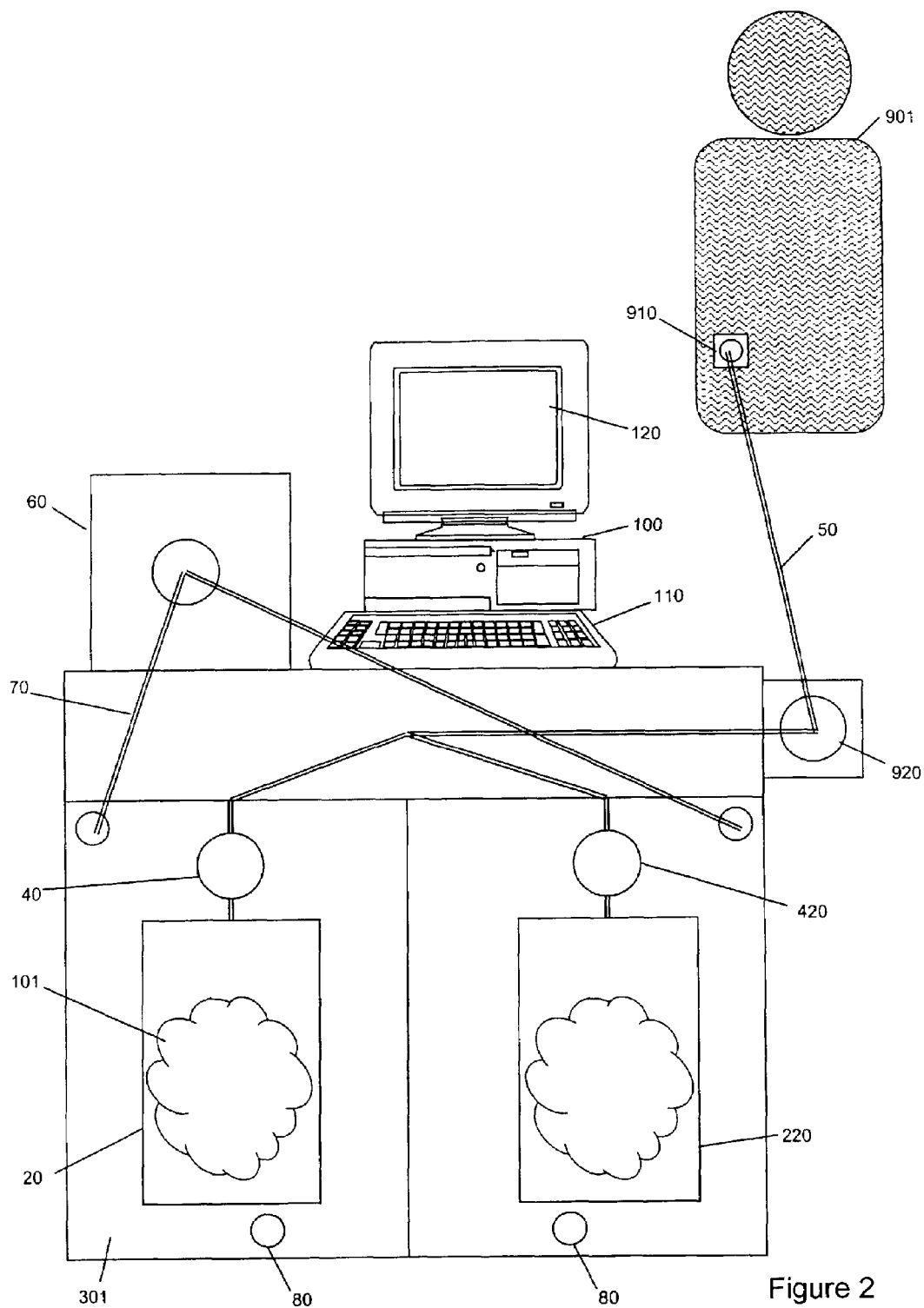
FIG. 2 is a schematic diagram of one embodiment of the present invention for use in a peritoneal dialysis process.

In a particular embodiment depicted in FIG. 2, a molded plastic cabinet housing is used and functions as the outer chamber 301 for the pump system of the present invention. The outer chamber 301 need not be a perfectly sealed chamber, and in fact may be perforated or otherwise open to the outside environment. This outer chamber 301 need only be configured such that the changes in pressure inside of it may be produced, measured and/or regulated.

As depicted in both FIG. 1 and FIG. 2, the outer chamber 30, 301 may be mounted on a standard load cell 40. The load cell 40 may be configured such that it can measure the flow of fluid 15, 101 into or out of the flexible chamber 20 and thus into or out of recipient or source 90, 901 of the fluid 15, 101. Also, depicted in FIGS. 1 and 2 is a tube 50, which may be any type of flexible or rigid tubing (such as standard medical tubing) or other such device providing a sealed passageway for the flow of fluids into or out of the flexible chamber 20, and which can be disposable. This tube 50 facilitates the flow of fluids 15, 101 into or out of the flexible chamber 20 as pressure is applied or withdrawn from the outer chamber 30, 301. In a particular embodiment, the tubes and flexible chamber may be sterile.

FIGS. 1 and 2 also depict a pressure reservoir 60, consisting of a vacuum pump or other source of increased or decreased pressure (as compared to that level of pressure surrounding the flexible chamber 20 disposed within the outer chamber 30, 301). This reservoir is provided for pressurizing, or drawing vacuum within the outer chamber to force the fluid 15, 101 in the system to flow into or out of the flexible chamber 20.

A transfer passageway 70, such as, for example, commercially available standard grade tubing, PVC tubing, or medical grade sterile tubing, can be used to transfer the pressure (or vacuum) from the pressure reservoir 60 into the outer chamber 30, 301.

An optional load cell 40 can be provided in various locations, such as, for example, outside of the outer chamber 30, 301, outside of the flexible chamber 20, or between the flexible chamber 20 and tube 50. This load cell 40 is configured such that it can measure the weight, mass, volume or other parameter of the chamber or chambers it is affixed thereto. This load cell 40 can provide feedback to an information processor 100, such as, for example, any computer, that may be provided to assist in regulating the fluid flow in this system.

An optional pressure valve 80 can be provided in various locations within the pressurized environment, such as, for example, within the transfer passageway 70 or outer chamber 30, 301, or disposed on the outside of the flexible chamber 20. This pressure valve 80 is provided to measure and assist in regulating the pressure applied to the outside of the flexible chamber 20.

It should be noted that the pressure reservoir 60 can be regulated or limited in a manner to avoid over pressurization of the system or recipient 90, 901 or flexible chamber 20 of the fluid 15, 101. This regulation may be particularly tailored for the properties of the fluid being pumped by, for example, the use of a computer.

The outer chamber 30 of at least one embodiment of the present invention is configured such that it isolates the flexible chamber 20 from atmospheric pressure. In this embodiment, as the outer chamber 30 pressure decreases, negative pressure is exerted on the flexible chamber 20, which causes fluid to move from an area of higher pressure (outside the pumping or delivering chamber), such as the target or reservoir 90, into the flexible chamber 20. Likewise, if the outer chamber 30 pressure increases, positive pressure is exerted on the flexible chamber 20, which causes fluid to move from an area of higher pressure (inside the flexible chamber 20), into the reservoir or target 90 set under lower pressure. The pressure in the outer chamber 20 is controlled by exposing the chamber to pressure reservoirs 60 that are regulated at specific positive or negative pressure (or vacuum) levels.

Figure 3:
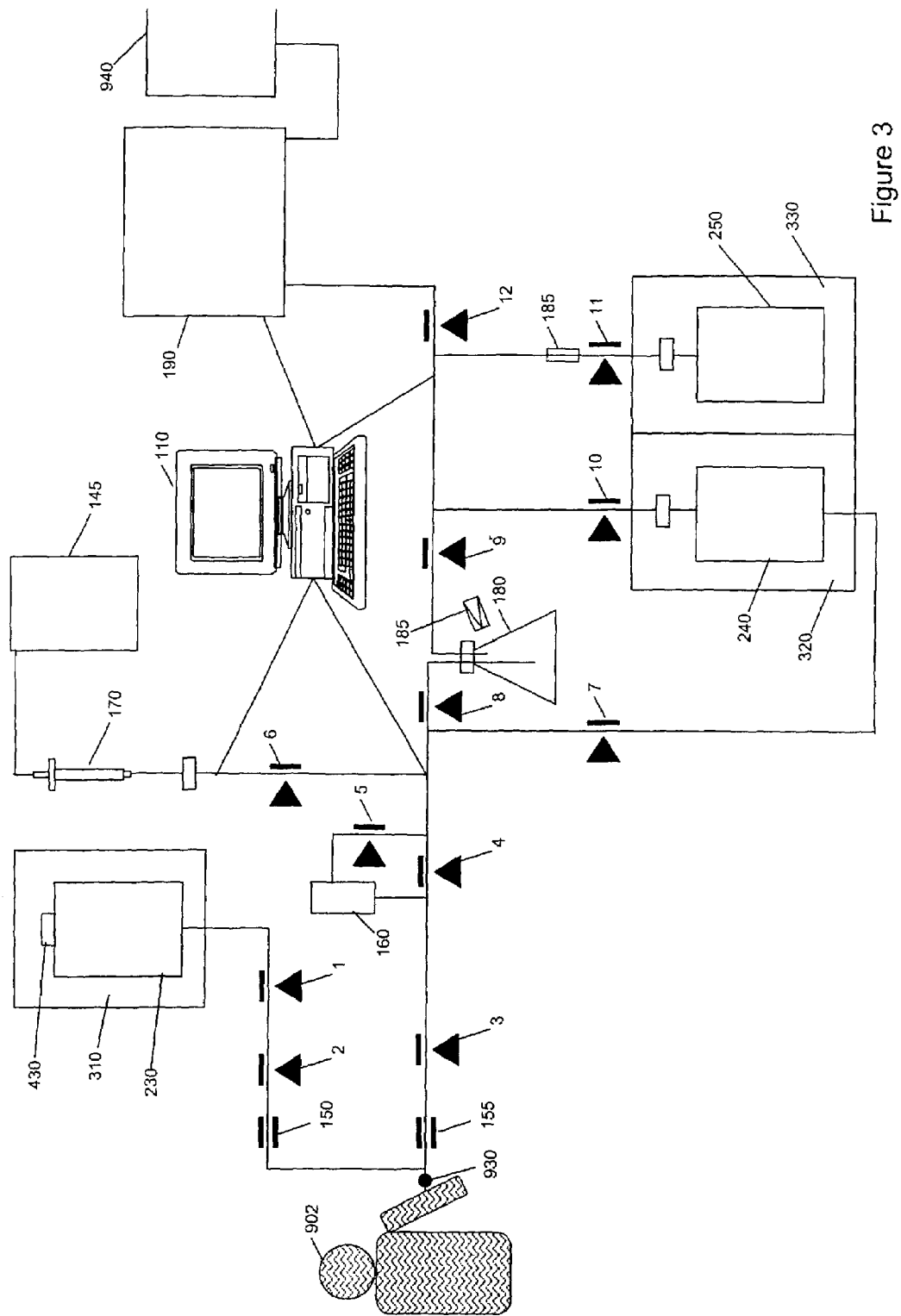
FIG. 3 is a schematic diagram of one preferred embodiment of the present invention for use in a photopheresis process.
Figure 4:
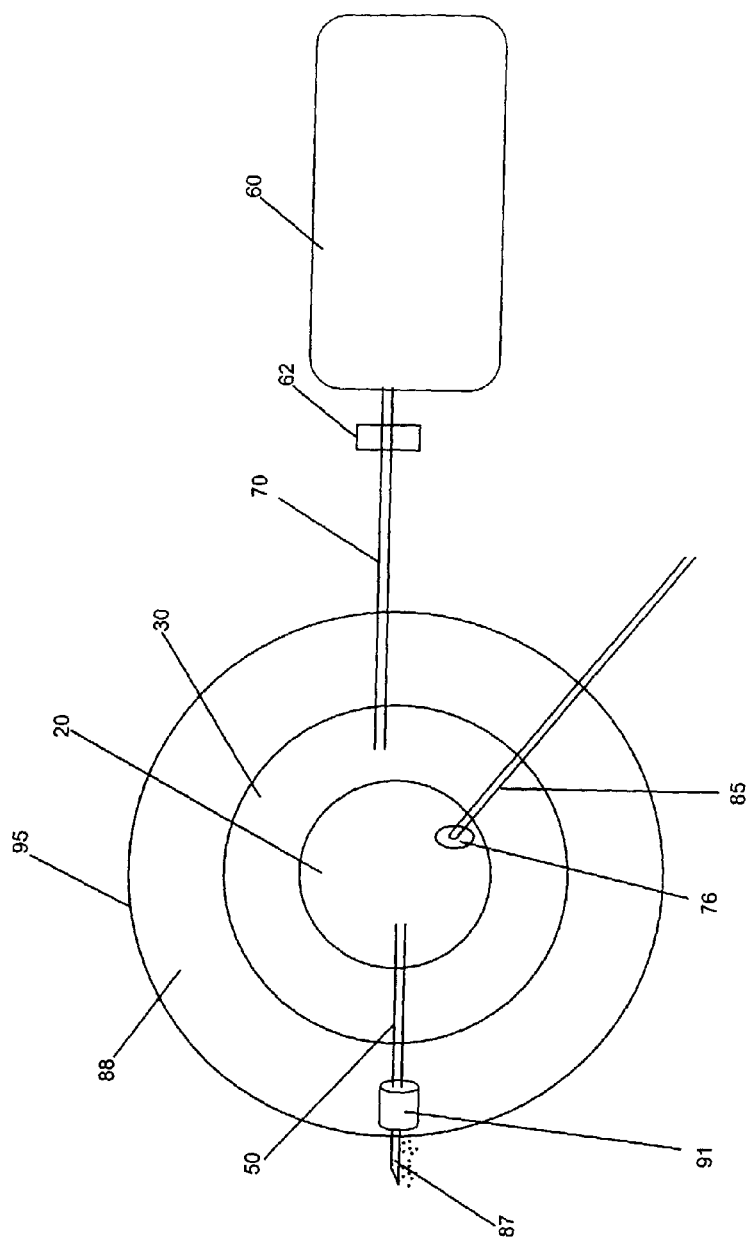
FIG. 4 is a schematic diagram of one embodiment of the present invention for use in a drug delivery process.

The following examples are intended to be purely exemplary of the invention. A first example, as depicted in FIGS. 3 and 5 through 9B, pertains to the use of the present invention in a photopheresis process. FIG. 4 pertains to the use of the present invention in a drug delivery process. FIG. 2 depicts the use of the present invention in, for example, a peritoneal dialysis process.

Light irradiation or phototherapy has been widely used in the chemical and biological sciences for many years. Light irradiation is the process of exposing targets, such as cells, to light energy. When the targets are microscopic or unable to stand-alone, a carrier (often times a fluid) is used to deliver the targets for irradiation. Exposing targets to light energy stimulates them and provokes them to undergo chemical or biological alterations.

In recent years, applications of phototherapy in the medical field, including patient therapy, are increasing. In such applications, the irradiation target could be, for example, a chemical molecule in clear solutions, viruses in blood, or blood cells suspended in plasma or other fluids.

Photopheresis involves extracting targets and then presenting the targets for phototherapy. In addition, phototherapy applications include using light energy to cause a photoactivatable drug to react with a target, specifically a target cell, and more specifically a white blood cell.

There are a number of applications of photopheresis. For example, photopheresis can be used as an antiviral treatment for certain blood components or whole blood. (See PCT Application WO 97/36634 entitled "Photopheresis Treatment of Chronic HCV Infections," which is expressly incorporated herein by reference). In this case, a pathogenic virus in a donated platelet concentrate can be eliminated by ultraviolet treatment (i.e., light energy therapy). Here, an ultraviolet-light activatable drug is added into a platelet concentrate bag and exposed to the ultraviolet light.

In another example, photopheresis can be used to treat cutaneous T-cell lymphoma ("CTCL"). (See PCT Application WO 97/36581 entitled "Photopheresis Treatment of Leukocytes," which is expressly incorporated herein by reference). In this photopheresis application, a patient ingests the drug 8-methoxypsoralen ("8-MOP") which, when mixed with a patient's blood, enters the nucleus of the white blood cells and weakly binds to the DNA. The lymphocytes or buffy coat (i.e., the doped white blood cells) are then extracted from the patient's blood and exposed to long-wave ultraviolet energy (i.e., ultraviolet A (UVA)). This exposure causes the photoactivated drug to lock across the cell nucleus. The locking disables the nucleus from replicating. The buffy coat is then returned to the patient. See also U.S. Pat. Nos. 4,838,852, 4,921,473, 5,150,705, 5,330,420, 5,383,847, 5,417,289, 5,433,738, 5,459,322, and 5,569,928, each of which is incorporated in its entirety herein by reference.

Figure 5:
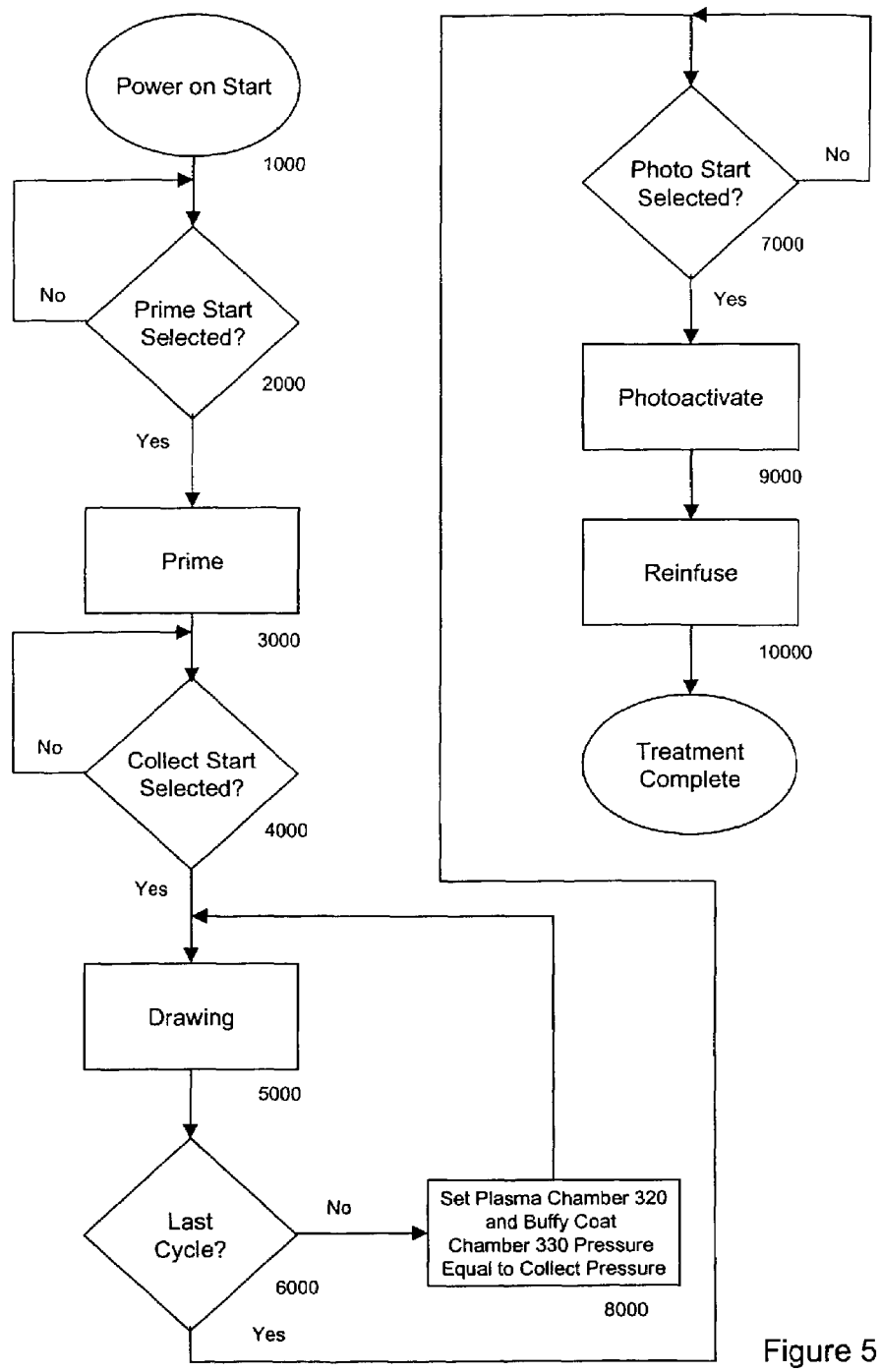
FIG. 5 is a flowchart diagram of one preferred embodiment of the process of the present invention for use in a photopheresis process.

FIG. 5 provides a flowchart of exemplary steps used with the present invention in an embodiment of a photopheresis process. The reference numbers used pertain to the diagram of FIG. 3. In FIG. 5 step 1000, the operator powers on the system, and then selects, in step 2000, prime from the control panel 110 to begin the photopheresis process. After priming the pump in step 3000, the operator selects collect start in step 4000 to begin drawing fluid in step 5000 from the patient through the pump. After a pre-determined number of cycles in step 6000, the operator then selects photo start in step 7000. If the pre-determined number of cycles has not been reached (preferably 1 to 9 cycles; more preferably, approximately 6 cycles) in step 8000, the operator sets the plasma chamber 320 and buffy coat chamber 330 pressure to equal the collect pressure and fluid is again drawn through the pump. The collect pressure is a negative pressure measurement set by the operator. The collected fluid, in this example, buffy coat, is processed in step 9000 by photoactivation. After the photoactivation process is complete, the fluid in step 10000 is then reinfused in to the patient and treatment is complete.

Figure 6A:
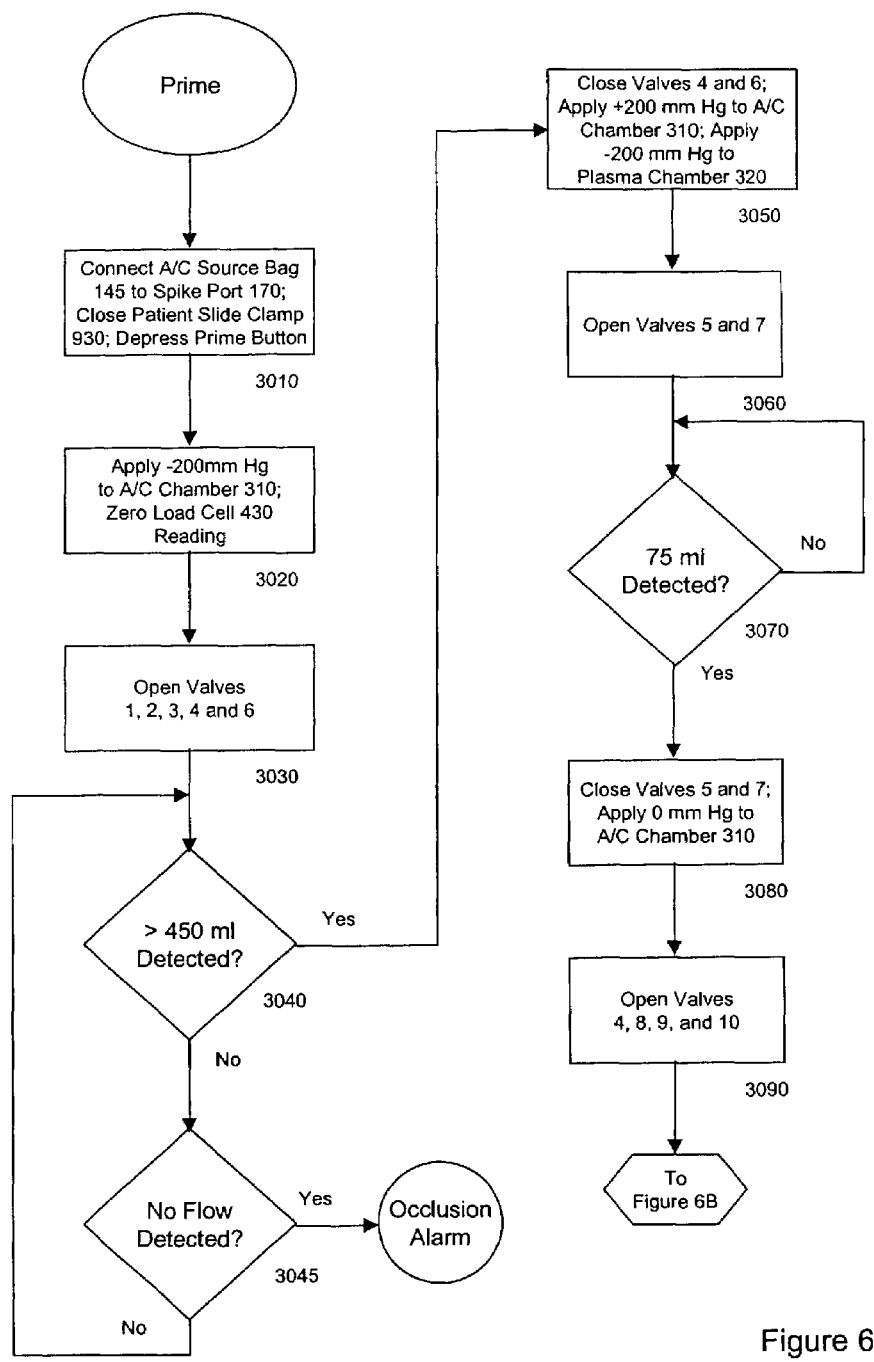
FIGS. 6A and 6B are a flowchart diagram of the priming process used in a preferred embodiment of the present invention for use in a photopheresis process.
Figure 6B:
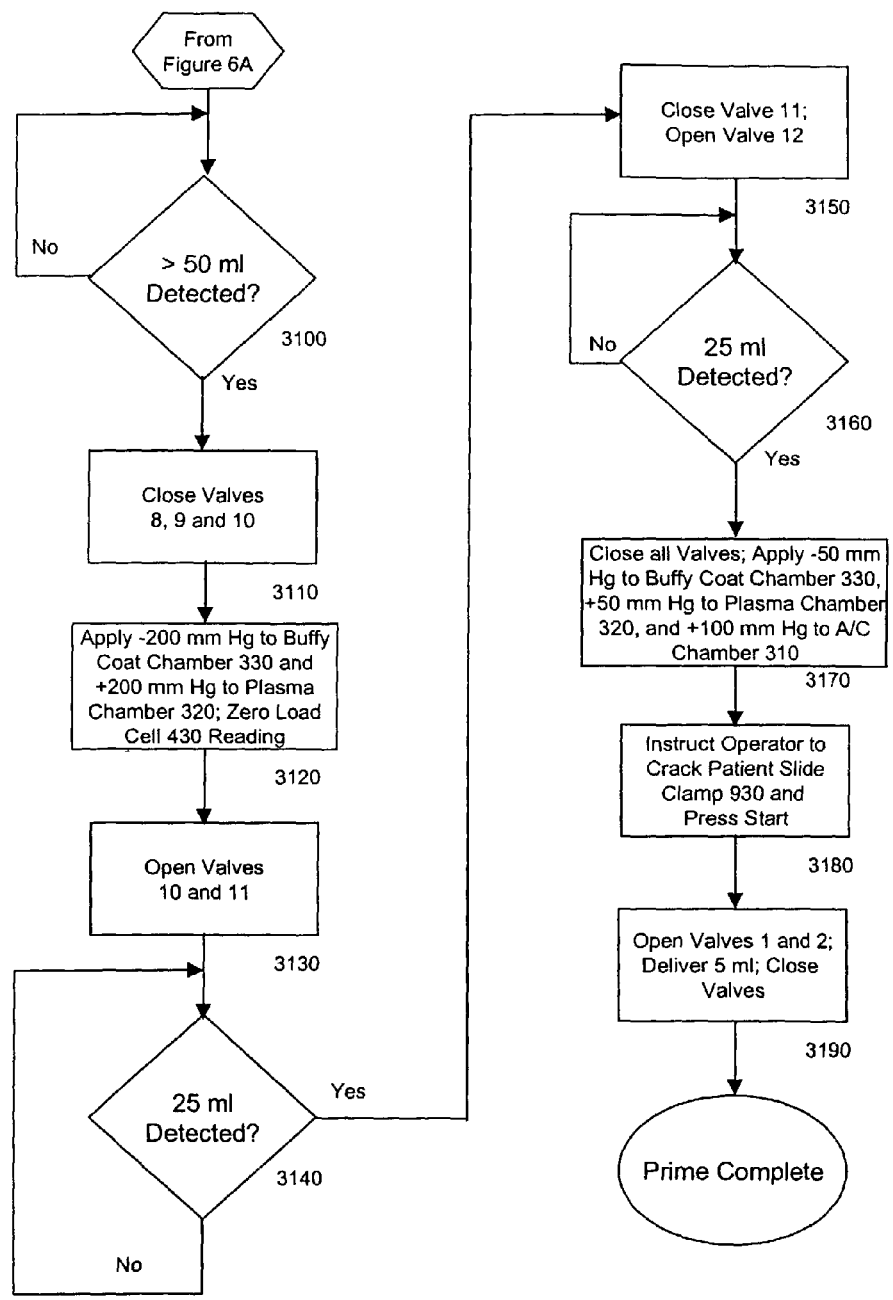

FIGS. 6A and 6B display the steps utilized to prime the pump from step 3000 of FIG. 5. First, in step 3000, the operator connects the A/C source bag 145 to the spike port 170, closes the patient slide clamp 930 and selects prime from the control panel 110. Air detectors 150, 155 of FIG. 3 are also energized to detect air in the system. Next, in step 3020, the system applies −200 mm Hg to the A/C chamber 310 and zeroes the load cell 430 reading. In step 3030, valves 1, 2, 3, 4 and 6 are opened, and fluid from the A/C source bag 145 begins to transfer through the spike port 170 to the A/C container 230. The system determines in step 3040 if less than 450 ml of fluid has been transferred. If less than 450 ml of fluid has been transferred, the system determines in step 3045 whether any fluid is indeed flowing. If no fluid transfer is detected, an occlusion alarm sounds. If fluid transfer is detected, then fluid transfer continues. When the fluid transfer level is greater than 450 ml, in step 3050, the system closes valves 4 and 6. Pressure is applied to the A/C chamber 310 (+200 mm Hg) and to the plasma chamber 320 (−200 mm Hg). The system then, in step 3060, opens valves 5 and 7 to allow fluid into the plasma container 240 bottom. Fluid flows into the plasma container 240 bottom until at least 75 ml of fluid is detected in step 3070. The system then closes off valves 5 and 7 in step 3080, and applies 0 mm Hg to the A/C chamber 310. The system in step 3090, opens valves 4, 8, 9 and 10 allowing fluid to enter the centrifuge bowl 180. When an amount of fluid greater than 50 ml has entered the centrifuge bowl 180 as determined in step 3100, the system closes valves 8, 9 and 10 in step 3110. Pressure is applied to the buffy coat chamber 330 (−200 mm Hg) and to the plasma chamber 320 (+200 mm Hg) in step 3120. The load cell 430 reading is zeroed again. Valves 10 and 11 are opened in step 3130 to permit fluid transfer from the plasma container 240 to the buffy coat container 250. When the fluid transfer level exceeds 25 ml, as determined in step 3140, the system closes valve 11 and opens valve 12 in step 3150, allowing fluid transfer from the plasma container 240 to the photoactivation plate 190. When the fluid level within the photoactivation plate 190 exceeds 25 ml, as determined in step 3160, the system closes all valves in step 3170. Pressure levels are set at −50 mm Hg in the buffy coat chamber 330, −50 mm Hg in the plasma chamber 320 and +100 mm Hg in the A/C chamber 310. The operator then primes access by cracking the patient slide clamp 930 and pressing start on the control panel 110 in step 3180. The system opens valves 1 and 2 in step 3190, delivering 5 ml of fluid and closes the valves to complete priming the pump. After the system draws the A/C source to the A/C container 230, the A/C source bag 145 is removed from the spike port 170 and replaced with a saline source bag.

Figure 7A:
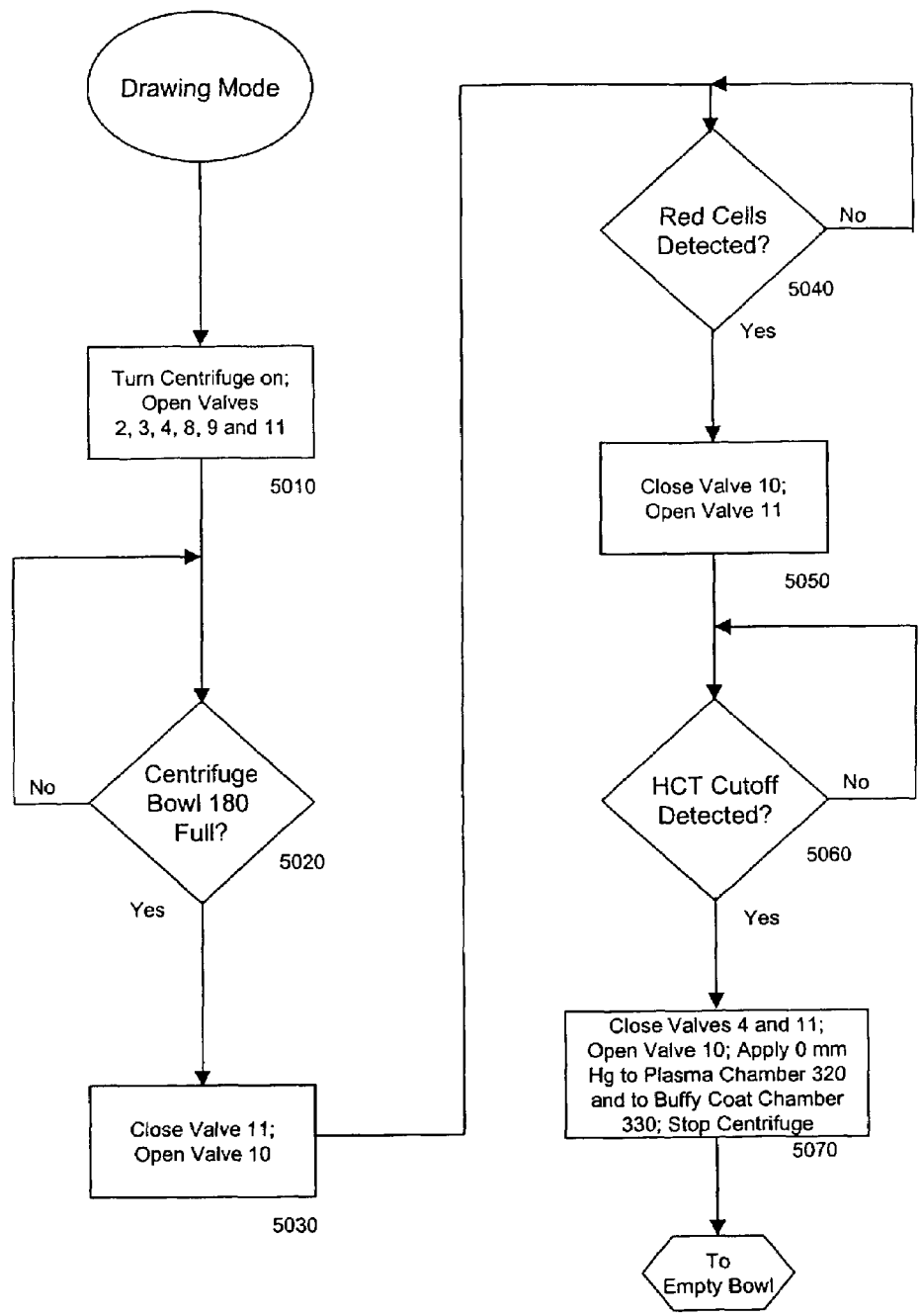
FIGS. 7A and 7B are a flowchart diagram of the drawing process used in a preferred embodiment of the present invention for use in a photopheresis process.
Figure 7B:
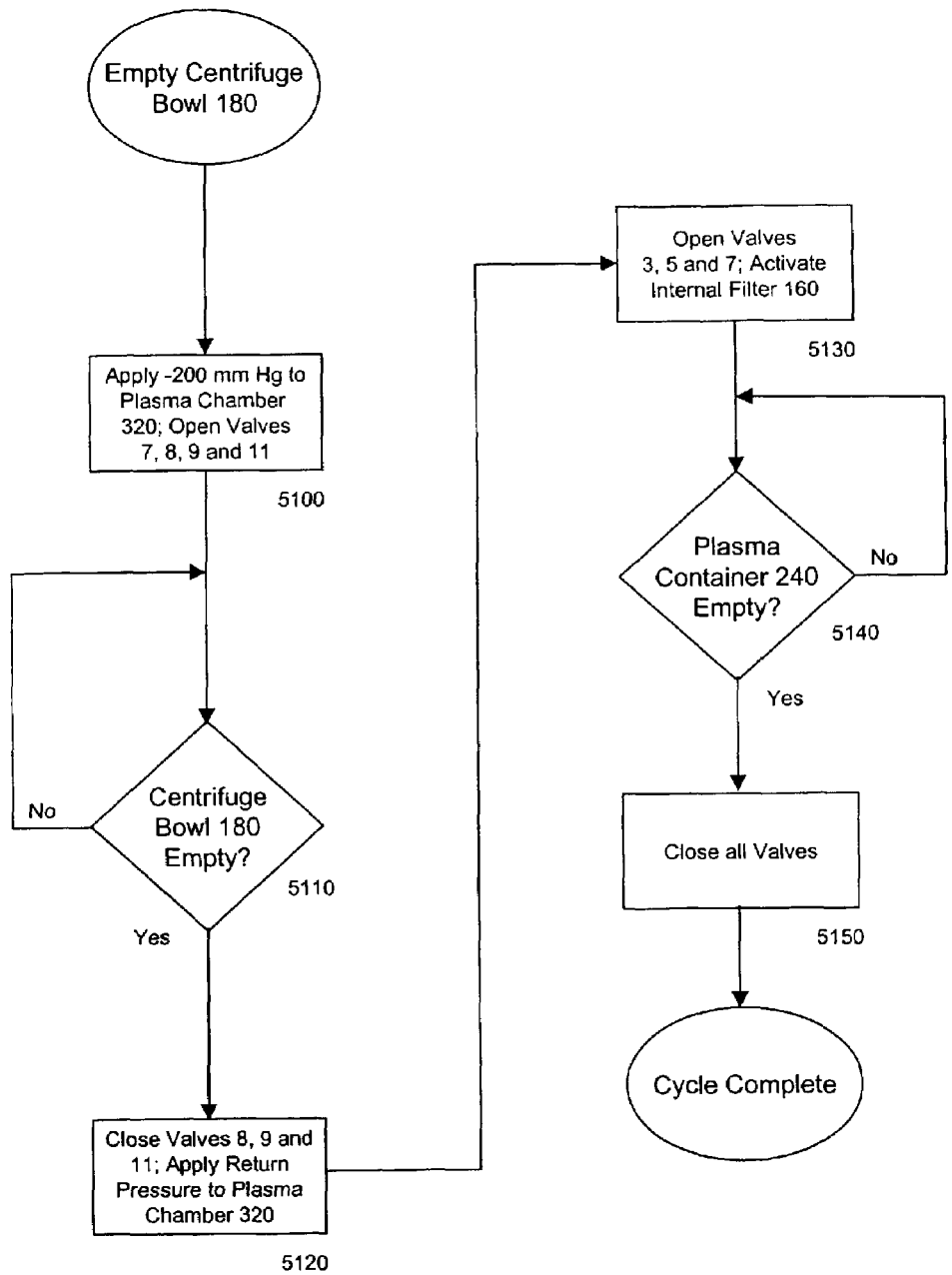

FIGS. 7A and 7B show the steps used to draw fluid from the patient 902 as described from step 5000 of FIG. 5 and as depicted diagrammatically in FIG. 3. When the operator depresses the collect start button on the control panel 110 in step 4000, the system in step 5010 turns the centrifuge on and opens valves 2, 3, 4, 8, 9 and 11, drawing the patient whole blood into the centrifuge bowl 180 while sterile air flows from the centrifuge bowl 180 to the buffy coat container 250. This process continues until the centrifuge bowl 180 is full as determined in step 5020. The system in step 5030 then closes valve 11 and opens valve 10. Plasma then flows from the centrifuge bowl 180 to the plasma container 240. An optic sensor 185 in the centrifuge bowl 180 is used to detect the presence of red cells in step 5040. When red cells are present, the system in step 5050 closes valve 10 and opens valve 11. The buffy coat is then collected in the buffy coat container 250. When a pre-determined HCT cutoff point is detected in step 5060 within the buffy coat container 250, the system in step 5070 closes valve 4 and 11, opens valve 10, sets the pressure of the plasma chamber 320 and the buffy coat chamber 330 to 0 mm Hg, and stops the centrifuge.

The system in step 5100 applies −200 mm Hg of pressure to the plasma chamber 320, then opens valves 7, 8, 9 and 11. Red cells that remained in the centrifuge bowl 180 flow into the plasma container 240 bottom and sterile air is pulled from the buffy coat container 250. When the centrifuge bowl 180 is empty, as detected in step 5110, the system in step 5120 closes valves 8, 9 and 11 and applies a return pressure to the plasma chamber 320. The return pressure is a positive pressure measurement set by the operator. In step 5130, valves 3, 5 and 7 are opened, and red cells and plasma are returned to the patient 902 via the internal filter 160. When the plasma container 240 is empty, as detected in step 5140, the system in step 5150 closes all valves and the drawing process is complete.

Figure 8:
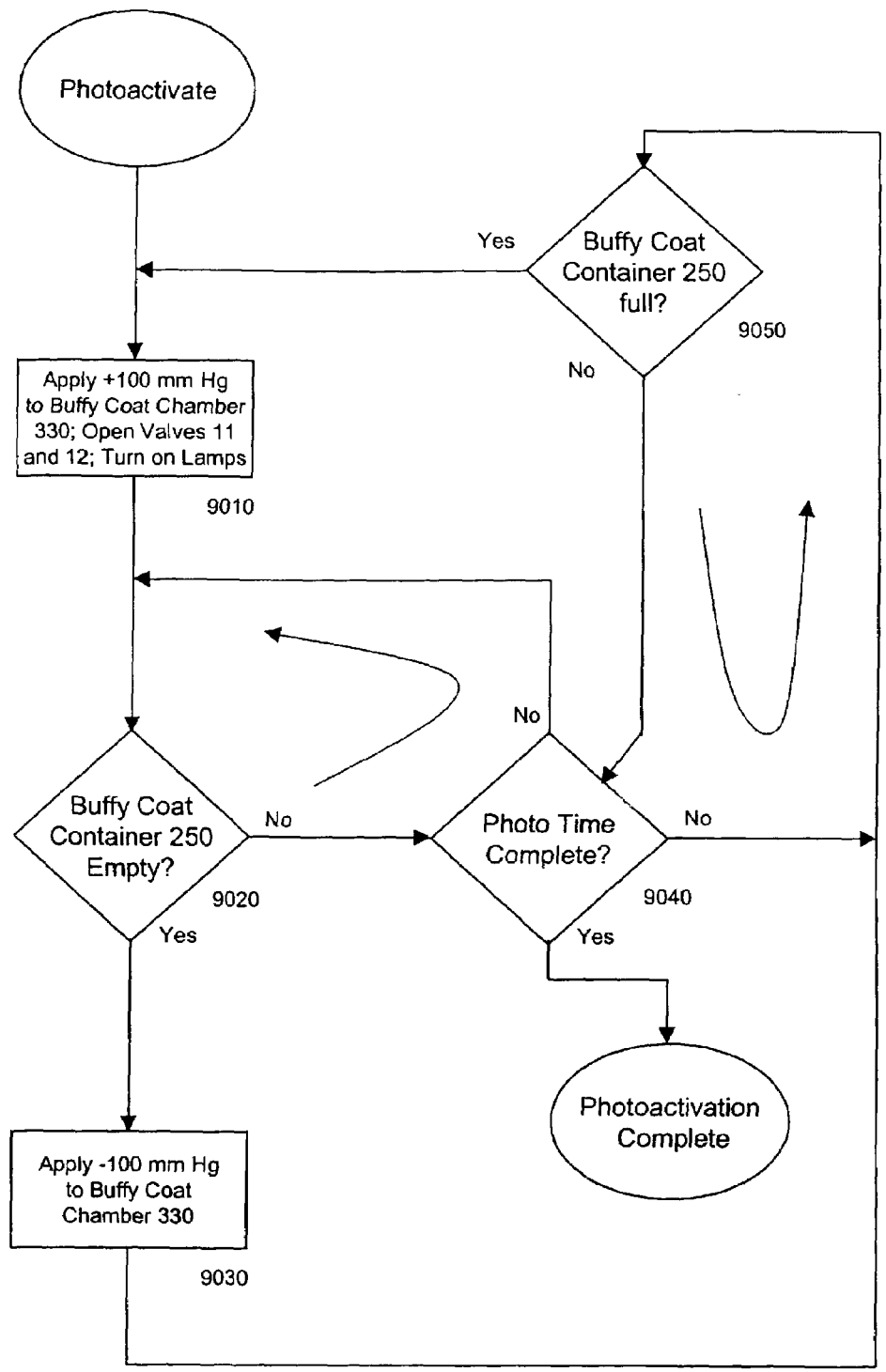
FIG. 8 is a flowchart diagram of the photoactivation process used in a preferred embodiment of the present invention for use in a photopheresis process.

In FIG. 8, the photoactivation process of step 9000 occurs when as detected in step 9050, the buffy coat container 250 is filed to a predetermined level. Then, in step 9010 the system applies +100 mm Hg of pressure to the buffy coat chamber 330 and opens valves 11 and 12. Buffy coat flows from the buffy coat container 250 to the receiver container 940 via the photoactivation plate 190. The system also activates the lamp, which treats the buffy coat with UVA energy as it flows through the photoactivation plate 190. When the buffy coat container 250 is empty, as detected in step 9020, the system in step 9030 applies −100 mm Hg of pressure to the buffy coat chamber 330 causing the buffy coat to flow from the receiver container 940 to the buffy coat container 250 via the photoactivation plate 190. This process is repeated for a predetermined time period, the end of which is determined in step 9040. The photopheresis process is then complete.

Figure 9A:
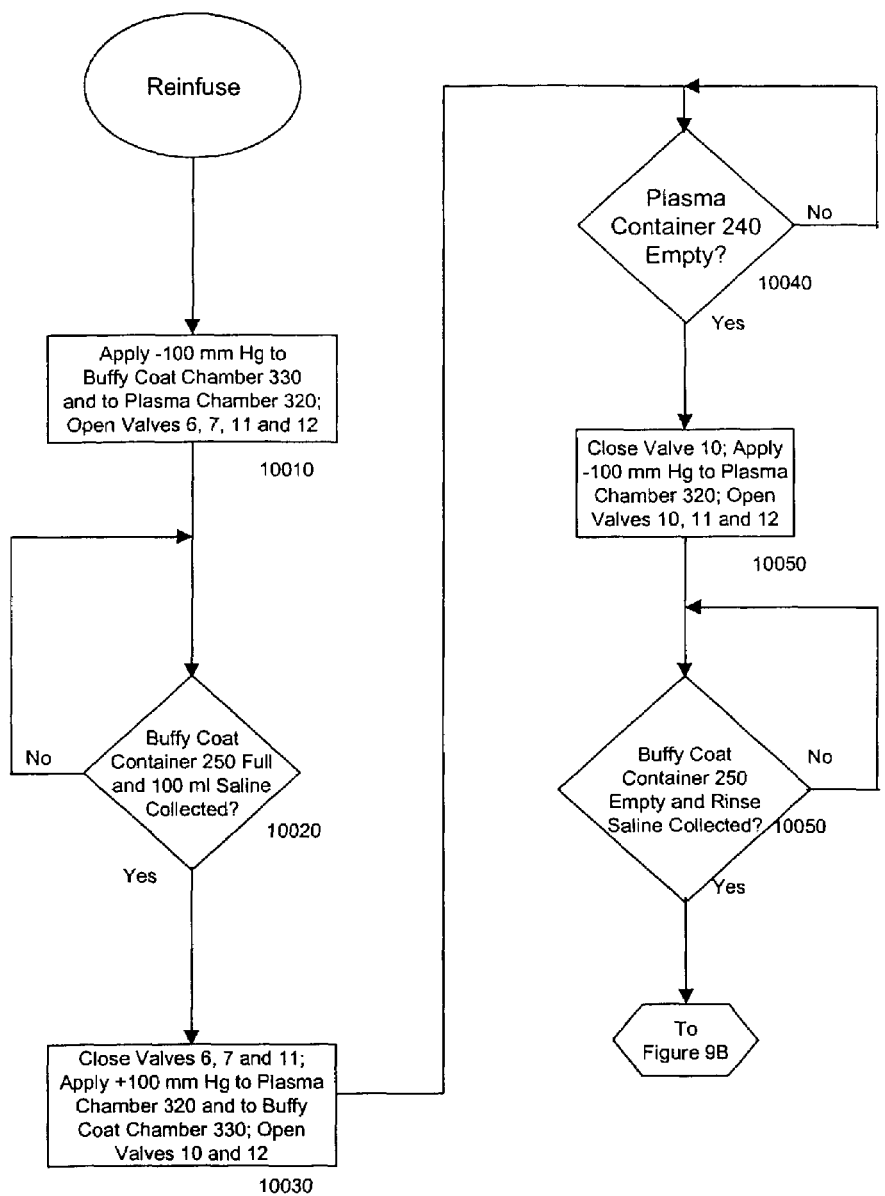
FIGS. 9A and 9B are a flowchart diagram of the reinfusion process used in a preferred embodiment of the present invention for use in a photopheresis process.
Figure 9B:
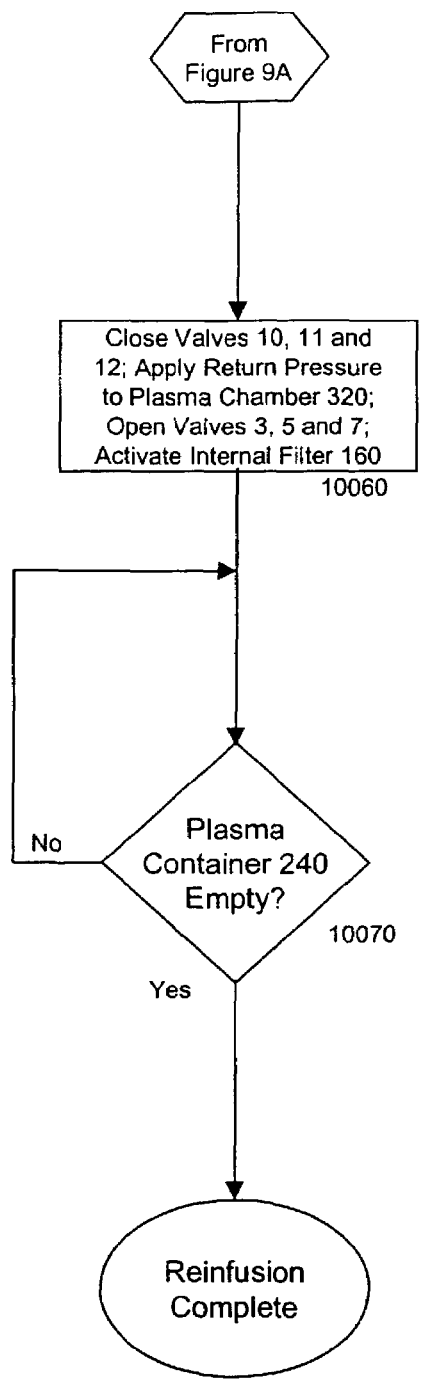

The treated buffy coat is then re-infused into the patient 902, which process is depicted, for example, in FIGS. 9A and 9B. The system in step 10010 applies −100 mm Hg of pressure to the buffy coat chamber 330 and the plasma chamber 320, and opens valves 6, 7, 11 and 12. Buffy coat then flows from the receiver container 940 via the photoactivation plate 190 into the buffy coat container 250, and saline flows into the plasma container 240. When the buffy coat container 250 is full and 100 ml saline has been collected in the plasma container 240 as detected in step 10020, the system in step 10030 closes valves 6, 7 and 11. Pressure is applied to the buffy coat chamber 330 and the plasma chamber 320 (+100 mm Hg). The system opens valves 10 and 12, allowing saline to rinse the photoactivation plate 190. When the plasma container 240 is empty as detected in step 10040, the system in step 10050 closes valve 10, applies −100 mm Hg of pressure to the plasma chamber 320, and opens valves 10, 11 and 12. Saline rinse fluid and buffy coat flow into the plasma container 240. When the buffy coat container 250 is empty as detected in step 10050, the system in step 10060 closes valves 10, 11 and 12, applies return pressure to the plasma chamber 320 and opens valves 3, 5 and 7. The return pressure is a positive pressure measurement set by the operator. Treated buffy coat and rinse fluid flows from the plasma container 240 into the patient 902 through the internal filter 160. When the plasma container 240 is empty as detected in step 10070 reinfusion is complete.

In another embodiment, the present invention may be used in a peritoneal dialysis process. Peritoneal dialysis uses the peritoneal membrane, which is the thin tissue surrounding the internal organs of the abdomen, as a dialysis filter. To prepare for peritoneal dialysis, a surgeon permanently places a catheter into the abdomen. The catheter is used to deliver the dialysate fluid into the peritoneal cavity, and after the peritoneal cavity is filled with the dialysate, toxins and excess water flow from the blood through the peritoneal membrane into the dialysate. After the waste products have diffused into the dialysate, the fluid is drained from the cavity through the catheter. The composition of the dialysate can be modified for individual needs with the major difference in dialysate formulae being the amount of dextrose used as the osmotic agent (e.g., 1.5, 2.5, or 4.25 g/dl). A commonly used type of peritoneal dialysis is continuous cyclic peritoneal dialysis ("CCPD").

In CCPD, a machine called a cycler is used to perform the fluid exchange which takes place at home overnight while the patient sleeps or is in a resting position. The cycler fills the peritoneal cavity with dialysate and allows it to dwell there for a prescribed amount of time before draining the fluid from the cavity. This technique offers freedom to the patient from daytime exchanges. As depicted in FIG. 2, the dialysate fluids 101 are loaded into the delivery/waste chamber 20 of the present invention. The fluids 101 are then heated to the delivery temperature, typically 37 degrees Celsius and maintained at that temperature under closed loop control throughout the treatment procedure. In this application, the flexible chamber 20 must be able to withstand the temperatures indicated and an apparatus for providing that temperature control must be incorporated into or in the vicinity of the flexible chamber 20 and/or outer chamber 301 or the heat may be provided by the same process that pressure is provided to the interior of the outer chamber 301 via tubing 70 or by some other well known transfer method.

The patient's treatment parameters (e.g., delivery flow rate, volume, dwell time, number of cycles) are programmed into an information processor 100 (such as, for example, a computer) via an operator and a control panel 110. Upon power up, the processor 100 can execute a power up self test. During the self test, the processor 100 automatically checks all sensors and actuators in the instrument, such as, for example, load cell 40 and/or pressure valve 80, as well as conducting internal verification that the electronics and microprocessors are functioning properly. After successful completion of the self test, a "ready to prime" message may be used as a prompt on the operator interface 120. When a prime button is depressed on the control panel 110, the processor 100 by, for example, controlling the opening of a clamp or valve 920, fills the fluid lines 50 with dialysate 101. The prime mode stops when fluid 101 reaches the distal end of the tubing 50.

Using standard aseptic technique, the patient 901 is connected to the administration set via their peritoneal catheter 910. The treatment initiates with a delivery cycle. Upon initiation of treatment, the delivery chamber 301 is pressurized to achieve a flow rate equal to the preset value. The flow rate is determined, for example, by monitoring the change in mass of the dialysate fluid 101 in the flexible chamber 20 via load cell 40. When the preset volume of fluid 101 is delivered, a supply clamp 920 closes, stopping the flow of fluid to the patient. Upon delivery of the preset volume, a countdown timer in processor 100 is started which counts down to the preset dwell time.

When the elapsed time equals the dwell time, a drain cycle is initiated. During the drain cycle, the pressure in the waste chamber 220 is reduced (under vacuum) to a pressure lower that that in the patient's peritoneal cavity 901, causing fluid 101 to move from the patient to the waste chamber 220. Waste chamber 220 is connected by tubing 50 to the patient 901 via the peritoneal catheter 910. The volume of fluid 101 collected in the waste chamber 220 is larger than the volume infused, the difference (ultrafiltrate) varying as a function of the dwell time and the osmotic gradient created by the (sugar) solutes added to the dialysate. The flow rate of dialysate 101 is controlled by varying the pressure within the chamber 301 to achieve the correct mass change (monitored by the processor 100) over time. The volume of dialysate 101 drained is monitored, for example, via load cell 420 and recorded.

The completion of the delivery, dwell and drain phases constitute one cycle. Under automatic control, the instrument cycles through the preselected number of cycles. After completion of the last cycle's drain phase, the processor 100 enters a standby state, which closes all line clamps and the control panel indicates the treatment is complete. The patient completes the treatment by disconnecting from the tube 50. At that time, tubing 50 and flexible chambers 20, 220 can be discarded.

In another embodiment, the pumps of the present invention may be used to deliver controlled amounts of various biological fluids, such as pharmaceuticals. For example, the pumps of the present invention may produce a significant improvement over the typical hypodermic injection in which a bolus of a biological fluid, such as insulin, is deposited in the body either from conventional hypodermic injectors or specially designed injectors. In such conventional methodologies, the bolus must be gradually absorbed and distributed throughout the body. This process is subject to many individual variances, including the physiology of the individual patient.

Thus, particularly with biological fluids such as insulin, interferon, erythropoietin, functional polypeptides, small molecules, antibodies, antigens, or oncotic agents, it may be preferable to have a continuous rate of infusion of the drug over a prolonged period of time (e.g., 24 hours or longer) rather than a number of injections within the same time period. Also, with certain active agents such as insulin, a diabetic may require a tonic or basal insulin level throughout the day, but after meals may require additional insulin to compensate for physiological changes caused by eating. Thus, the pump of the present invention may preferably be provided with means for increasing biological fluid flow, decreasing biological fluid flow, and/or imposing a pulse dosage, such means preferably controllable by the patient or health care provider.

As shown, for example, in FIG. 4, the pumps of the present invention can be used in a biological fluid delivery system. As with the previously described embodiments, the sealed flexible chamber 20 is disposed within an outer chamber 30. Flexible chamber 20 is adapted to contain biological fluids for delivery to one in need thereof. For example, the biological fluid may be insulin for delivery to a diabetic patient. The sealed flexible chamber 20 is preferably sterile and may be pre-packaged with the biological fluid to be pumped or delivered. The outer chamber 30 of FIG. 4 surrounds the flexible chamber 20 and may comprise a plastic or other molded housing or other type container, such as, for example, might be used to house a medical device, or may be a molded plastic cassette. The outer chamber 30 may, in an alternative embodiment, also be surrounded by a housing 88. The housing 88 may serve to protect the outer chamber 30 and inner chamber 20, as well as providing means for attaching the pump to a surface or directly to a patient through use, for example, of an adhesive overlay 95 or other conventional attachment means. In a preferred embodiment, the adhesive overlay 95 is placed on the base of the pump and may also serve as a carrier for a topical antiseptic, antibiotic, or other agent for reduction of the possibility of infection or patient discomfort.

Each of the outer chamber 30 and the housing 88 preferably may be molded in one piece from a transparent material such as polymethlymethacrylate, polycarbonate, polysulfone, PVC, medium to high density polyethylene or other transparent or semi-transparent high modulus polymers which are heat resistant, chemically inert, and preferably capable of withstanding sterilization conditions. Visual confirmation of the operational status of the pumps of the present embodiment may be facilitated by having the flexible chamber 20, outer chamber 30 and the optional housing 88 constructed of such semi-transparent or transparent materials. The flexible chamber 20 may be provided with a septum 76, inserted through an opening in flexible chamber 20, outer chamber 30 and optionally housing 88, in sealing engagement therewith and adapted to be re-sealingly pierced by an inlet port 85, which may comprise, for example, a needle and associated cannula, for filling or adding biological fluid to the flexible chamber 20. For example, a needle could be attached to inlet port 85 with the inner end of the needle being of sufficient length to pierce septum 76 and provide a re-sealable fluid passageway from the interior of chamber 20 to the exterior of the pump.

Outlet port 50, which may be any type of flexible or rigid tubing (such as standard medical tubing) or other such device, provides a sealed passageway for the flow of fluids into or out of the flexible chamber 20, and can be disposable. This outlet port 50 facilitates the flow of fluids out of the flexible chamber 20 and into the patient as pressure is increased or decreased in the outer chamber 30. While the outlet port 50 may comprise an integral needle which facilitates the direct insertion and attachment of the pump to a patient at the site of the pump, the outlet port 50 may alternatively comprise an attachment means 91 for attaching the outlet port 50 to a conventional cannula, catheter, IV-line or needle, which may be inserted into the patient at an area remote from that on which the pump is placed. Such a cannula may be connected to the outlet port 50 at one end and the other end may have a needle inserted directly into the patient or may be attached to other apparatus such as conventional IV-set by a Y-fitting so that the dosage delivered from the pump may be superimposed on another dosage form. Alternatively, the outlet port 50 may be connected to a nasopharyngal tube to administer the biological fluid to a patient's gastrointestinal tract or connected to a Foley catheter for delivery of the biological fluid to the bladder.

FIG. 4 also depicts a pressure reservoir 60 provided for pressurizing the outer chamber 30 to force the biological fluid out of the flexible chamber 20. A transfer passageway 70, such as, for example, commercially available standard grade tubing, PVC tubing, or medical grade sterile tubing, can be used to transfer the pressure (or vacuum) from the pressure reservoir 60 into the outer chamber 30.

As noted above, the pressure reservoir 60 can be regulated or limited in a manner to avoid over pressurization of the flexible chamber 20. This regulation may be particularly tailored for the properties of the biological fluid being pumped by, for example, the use of a computer.

Indeed, as the outer chamber 30 pressure increases, positive pressure is exerted on the flexible chamber 20, which causes the biological fluid to move from an area of higher pressure (inside the flexible chamber 20) into the outlet port 50. The pressure in the outer chamber 30 may be controlled through pressure reservoir 60. The pressure reservoir may be regulatable by the patient or health care provider, or it may be fixed at a specific pressure level. In regulating the flow of the biological fluid into the patient, it may be preferable to reduce the flow of the biological fluid into the patient or, alternatively, provide a pulse or bolus of biological fluid to the patient. To reduce the flow, one may decrease the outer chamber 30 pressure. When less pressure is exerted on the flexible chamber 20, less fluid moves from the flexible chamber 20 to the patient. Likewise, to increase the flow, one may increase the outer chamber 30 pressure.

The administration rate typical of drugs such as insulin, interferon, various functional polypeptides, small molecules, antibodies, antigens and oncotic agents, which are generally administered through the skin into the subcutaneous space, is relatively minute, e.g., approximately 5 milliliters or less per day. With this design approach, a small, compact pump can be provided which can administer not only a single day's supply, but also a multi-day or week's supply. Five milliliters per day can be delivered by a flow rate of only slightly more than 0.2 milliliters per hour, a delivery rate well within the capability of the present pumps.

In a particular embodiment, the components of the pump may be delivered in a partially assembled and sterile condition.

Various embodiments of the pumps of the present invention, utilized for delivery of a biological fluid, can have different flow rates determined by the type of drug, the dosage of the drug and the specific design or size of the pump itself. It is contemplated that the partially assembled device would comprise the flexible chamber 20 surrounded by the outer chamber 30. The flexible chamber 20 may have associated with it, in fluid communication thereof, an outlet port 50 and an optional inlet port 85 and septum 76. In this embodiment, the prepackaged pumps may be provided in sterile form to the patient or health care provider to assemble the appropriate combinations.

Since the pump of the present invention can continuously deliver a biological fluid, e.g., insulin, for the same time period that now requires many pulse injections, the advantages of this system are readily apparent. In addition, when a pulse dosage form is used in combination with the pump assembly, pulse dosages can be administered to supplement the tonic basal delivery rate of the pump without the necessity of an additional puncture for each pulse. Indeed, it is contemplated that the pumps of the present invention are configured so that differing outputs may be achieved so that the desired flow rate for any particular biological fluid can be obtained. This may be accomplished by control of the pressure reservoir 60 through pressure controlling means 62. Controlling means 62 may comprise any conventional valving means that allows a user to accurately control the pressure from the pressure reservoir to the outer chamber 30. Further adjustment of the flow rate is possible by providing means for opening or closing the outlet port 50 once pressure is applied to the flexible chamber 20.

In another embodiment, one may fill the flexible chamber 20 through inlet port 85 by any appropriate means, e.g. with a sterile needle, with the appropriate biological fluid for delivery to a patient. Once filled, the inlet port 85 is preferably sealed from the flexible chamber 20 in order to ensure that the only subsequent flow of biological fluids from the flexible chamber 20 occurs through the outlet port 50. The flexible chamber 20 may then be pressurized by the pressure reservoir 60. The biological fluid is then forced through the outlet port 50 and through cannula or needle 87. When a steady flow of fluid is seen to be emerging from the needle 87 it may then be inserted under the skin of the patient. While the above embodiment contemplates the filling of the pump assembly through input port 85, it is also contemplated that the input port 85 can be eliminated and the biological fluid to be dispensed provided in modular form. Thus, for example, the biological fluid to be dispensed may be provided within the flexible chamber 20 in prepackaged form together with or separate from a pressure reservoir 60 which may be pre-calibrated to produce any desired flow rate of the biological fluid for any desired duration.

The pump assembly may preferably be sized to be easily concealed under the clothing and to present a relatively innocuous and non-disfiguring appearance to assist in the subjective acceptance of the device by the user, for example, when attached directly to the user by adhesive overlay 95.

In a specific example, the known Kamen-type pump technology is compared with an embodiment of the continuous flow pump methodology of the present invention (as described, for example, in FIG. 3), in a known photopheresis system (e.g., the UVAR® XTS™ system). Whole blood is obtained from a donor source, anti-coagulant is added, and the concentration and number of white blood cells in the donor blood is preferably then determined. The donor blood is then divided into two equal aliquots. One of the aliquots is pumped into the centrifuge of, for example, a UVAR® XTS™ system using the Kamen pump technology. The other aliquot is pumped into the centrifuge of the same type of system, yet using a embodiment of the continuous pump of the present invention. Once centrifuged, the buffy coat fraction resulting from each experiment is isolated and measured for red blood cell contamination (% hematocrit and number of cells) and white blood cell concentration. The elapsed treatment (collection) time for each experiment is also measured, i.e., the time it takes to collect and separate the donor blood within the process of each system.

In comparing the use of the pump of the present invention with the use of the Kamen type pump in the XTS™ system, it is determined that use of the pump of the present invention provides for one or more of: a reduction in total treatment or process time for the donor blood in the XTS™ system; a reduction in irradiation time of collected buffy coat in the system; an increased flow rate of whole blood into the system, as well as collected buffy coat out of the centrifuge of the XTS™ system; an increased total number of target cells (e.g., white blood cells) collected or separated per total white blood cells contained in the donor blood (i.e., yield); an increased total number of target cells collected per treatment or per unit process time; an increased number of total white blood cells collected per total volume of processed donor blood; a reduction of the contamination of collected white blood cells collected (e.g., an increase the percentage of white blood cells collected per total cells collected and/or decreasing the percent hematocirt in the collected buffy coat); and a reduced pressure differential and a reduce flow rate differential within the extracorporeal circuit.

In another specific example, the known peristaltic pump technology is compared to an embodiment of the continuous flow pump methodology of the present invention (as described, for example, in FIG. 3), in a known photopheresis system (e.g., the UVAR® system). Whole blood is obtained from a donor source, anti-coagulant is added and measured for free hemoglobin. The donor blood is then divided into two equal aliquots. One of the aliquots is continuously recycled from the aliquot source through the pump of a UVAR® system using a conventional peristaltic pump. The other aliquot is continuously recycled from the aliquot source through the pump of the same type of system, yet using a embodiment of the continuous pump of the present invention. Each aliquot is recycled through the pump approximately 50 times. At the completion of the pumping cycles, each aliquot is measured for free hemoglobin.

In comparing the use of the pump of the present invention with the use of a peristaltic type pump in the UVAR® system, it is determined that use of the pump of the present invention provides for a reduction in cell (red blood cell) damage (e.g., reduced hemolysis), as well as one or more of the improvements found in the comparison of the pumps and methods of the present invention with the Kamen-type pump in the UVAR® XTL™ system.

It will be apparent to those skilled in the art that various modifications and variations can be made in the method and apparatus of the present invention and in construction of the pump system and apparatus of the present invention without departing from its scope or spirit. As an example, the method and apparatus of the present invention can be applied to any use that mandates uninterrupted flow, such as but not limited to photopheresis, cell separation, or dialysis. It also can be used to provide a means for more simply moving fluids, and in particular pressure or flow sensitive fluids, such as in cyclical peritoneal dialysis systems, and other drug delivery systems, bypass and other blood flow systems, and methods and systems for manufacturing sensitive and/or sterile fluids, as well as biological fluids.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for providing substantially stable flow of a biological fluid comprising:
    an outer chamber adapted to contain a sealed flexible chamber, wherein said outer chamber is adapted to provide a space containing a pressure sensitive medium around said sealed flexible chamber;
    said sealed flexible chamber adapted to contain fluid, wherein said sealed flexible chamber comprises a fluid path between said sealed flexible chamber and an exterior of said outer chamber;
    a receiving container that is in fluid communication with said sealed flexible chamber via a photoactivation element, and is adapted for returning said fluid from said receiving container to said sealed flexible chamber;
    a pressure reservoir adapted for continuously increasing or decreasing the pressure in a uniform and controlled manner within said space around said sealed flexible chamber;
    a pressure valve adapted for continuously increasing or decreasing the pressure in a uniform and controlled manner within said space around said sealed flexible chamber, wherein said apparatus renders said biological fluid suitable for return to a patient; and
    means for monitoring the properties of fluid displaced into or out of said sealed flexible chamber, wherein said means for monitoring comprises a load cell.

2. An apparatus for providing substantially stable flow of a biological fluid comprising:
    a sealed flexible chamber adapted to contain fluid disposed within an outer chamber, wherein said sealed flexible chamber comprises a fluid path between said sealed flexible chamber and the exterior of said outer chamber and wherein said outer chamber is adapted to provide a space containing a pressure sensitive medium around said sealed flexible chamber;
    means for continuously increasing or decreasing the pressure in a uniform and controlled manner within said space around said sealed flexible chamber;
    means for changing the pressure within said space around said sealed flexible chamber such that fluid is displaced into or out of said sealed flexible chamber in a uniform and controlled manner, wherein said apparatus renders said biological fluid suitable for return to a patient; and
    a receiving container that is in fluid communication with said sealed flexible chamber via a photoactivation element, and is adapted for returning said fluid from said receiving container to said sealed flexible chamber;
    wherein said apparatus is adapted for use in conjunction with a photopheresis process that comprises collecting a buffy-coat fraction of said biological fluid; adding a photoactivatable drug to said buffy-coat fraction; exposing said buffy-coat fraction to light energy; and reinfusing said exposed buffy-coat fraction.

3. The apparatus of claim 2, wherein said buffy-coat fraction comprises white blood cells.

4. The apparatus of claim 2, wherein said photoactivatable drug is 8-methoxyp-soralen.

5. The apparatus of claim 2, wherein said light energy comprises ultraviolet A.

* * * * *